(12) United States Patent
Yue

(10) Patent No.: US 7,207,715 B2
(45) Date of Patent: Apr. 24, 2007

(54) METHOD TO IMPLEMENT FULL SIX-DEGREE TARGET SHIFT CORRECTIONS IN RADIOTHERAPY

(75) Inventor: Ning J. Yue, Gibsonia, PA (US)

(73) Assignee: UPMC, Pittsburgh, PA (US)

( * ) Notice: Subject to any disclaimer, the term of this patent is extended or adjusted under 35 U.S.C. 154(b) by 0 days.

(21) Appl. No.: 11/192,875

(22) Filed: Jul. 29, 2005

(65) Prior Publication Data

US 2007/0025524 A1    Feb. 1, 2007

(51) Int. Cl.
*A61B 6/08* (2006.01)

(52) U.S. Cl. .................................................... 378/205
(58) Field of Classification Search ............... 378/205, 378/204, 206
See application file for complete search history.

(56) References Cited

U.S. PATENT DOCUMENTS

| | | | | |
|---|---|---|---|---|
| 5,622,187 | A * | 4/1997 | Carol | 128/897 |
| 6,032,066 | A * | 2/2000 | Lu et al. | 600/407 |
| 6,535,574 | B1 * | 3/2003 | Collins et al. | 378/65 |
| 6,574,356 | B1 * | 6/2003 | Lee et al. | 382/131 |
| 6,973,202 | B2 * | 12/2005 | Mostafavi | 382/103 |
| 2002/0122534 | A1 * | 9/2002 | Polkus et al. | 378/205 |
| 2004/0122311 | A1 * | 6/2004 | Cosman | 600/427 |
| 2005/0234327 | A1 * | 10/2005 | Saracen et al. | 600/407 |
| 2006/0215813 | A1 * | 9/2006 | Scherch et al. | 378/65 |

OTHER PUBLICATIONS

Intensity Modulated Radiation Therapy Collaborative Working Group, "Intensity modulated radiotherapy: Current status and issues of interest", Int. J. Radiat. Oncol. Biol. Phys., 51, 880-914 (2001).

Rudat, V. et al., "Combined error of patient positioning variability and prostate motion uncertainty in 3D conformal radiotherapy of localized prostate cancer", Int. J. Radial. Oncol. Biol. Phys., 35, 1027-1034 (1996).

Roach, III, M. et al., "Prostate volumes and organ movement defined by serial computerized tomographic scans during three-dimensional conformal radiotherapy", Radiat. Oncol. Invest. 5, 187-194 (1997).

Mackie, Thomas R. et al., "Image guidance for precise conformal radiotherapy", Int. J. Radiat. Oncol. Biol. Phys., 56, 89-105 (2003).

Lattanzi, J. et al., "A comparison of daily CT localization to a daily ultrasound-based system in prostate cancer", Int. J. Radiat. Oncol. Biol. Phys., 43, 719-25 (1999).

Mubata, C.D. et al., "Portal imaging protocol for radical dose-escalated radiotherapy treatment of prostate cancer", Int. J. Radiat. Oncol. Biol. Phys., 40, 221-231 (1998).

Alasti, Hamideh et al., "Portal imaging for evaluation of daily on-line setup errors and off-line organ motion during conformal irradiation of carcinoma of the prostate", Int. J. Radiat. Oncol., Biol. Phys., 49, 869-884 (2001).

(Continued)

*Primary Examiner*—Courtney Thomas
*Assistant Examiner*—Alexander Taningco
(74) *Attorney, Agent, or Firm*—Thomas C. Wettach, Esq.; Cohen & Grigsby, P.C.

(57) ABSTRACT

The invention provides a method using matrix transformations of the three coordinate systems used in radiotherapy to correct for any deviation between a planned dosimetric treatment target and the actual location of the treatment target.

4 Claims, 9 Drawing Sheets

OTHER PUBLICATIONS

Balter, James M. et al., "Determination of ventilatory liver movement via radiographic evaluation of diaphragm position", Int. J. Radiat. Oncol. Biol. Phys., 51, 267-270 (2001).

Balter, James M. et al., "Online repositioning during treatment of the prostate: a study of potential limits and gains", Int. J. Radiat. Oncol. Biol. Phys., 27, 137-143 (1993).

Swindell, William, "A 4-MV CT scanner for radiation therapy: spectral properties of the therapy beam", Med. Phys. 10, 347-351 (1983).

Ruchala, K.J. et al., "Megavoltage CT image resconstruction during tomotherapy treatments", Physics in Medicine & Biolog, 45, 3545-3562 (2000).

Siewerdsen, Jeffrey H. et al., "Cone-beam computed tomography with a flat-panel imager: magnitude and effects of x-ray scatter", Med. Phys., 28, 220-231 (2001).

Mackie, T. Rock et al., "Tomoherapy: a new concept for the delivery of dynamic conformal radiotherapy", Med. Phys., 20, 1709-1719 (1993).

Mageras, Gig S. et al., "A method of incorporating organ motion uncertainities into three-dimensional conformal treatment plans", Int. J. Radiat. Oncol. Biol. Phys. 35, 333-342 (1996).

Yan, Di et al., "Adaptive modification of treatment planning to minimize the deleterious effects of treatment setup errors", Int. J. Radiat. Oncol. Biol. Phys. 16, 197-206 (1997).

Keller, Harry et al., "Optimal stochastic correction strategies for rigid-body target motion", Int. J. Radiat. Oncol. Biol. Phys., 55, 261-270 (2003).

Adler, Jr., John R. et al., "The Cyberknife: a frameless robotic system for radiosurgery", Stereotactic and Functional Neurosurgery 69: 124-128 (1997).

Yin, Fang-Fang et al., "Dosimetric characteristics of Novalis shaped beam surgery unit", Med. Phys. 19: 1729-1738 (2002).

Siddon, Robert L., "Solution to treatment planning problems using coordinate transformation", Med. Phys. 8(6), 766-774 (1981).

Bond, James E. et al., "Comparison of an image registration technique based on normalized mutual information with a standard method utilizing implanted markers in the staged radiosurgical treatment of large arteriovenous malformations", International Journal of Radiation Oncology, Biology, Physics, 57(4): 1150-8, 2003.

Yue, Ning J. et al., "A technique to reestablish dose distributions for previously treated brain cancer patients in external beam radiotherapy", Med. Dosi., 29 (1): 31-41, 2004.

Litzenberg, Dale W., "A mathematical model for correcting patient setup errors using a tilt and roll device", Med. Phys. 26 (12), 2586-2588, Dec. 1999.

Court, Laurence et al., "Evaluation of mechanical precision and alignment uncertainties for an integrated CT/LINAC system", Med. Phys. 30 (6), 1198-1210, Jun. 2003.

* cited by examiner

Rotate 90°

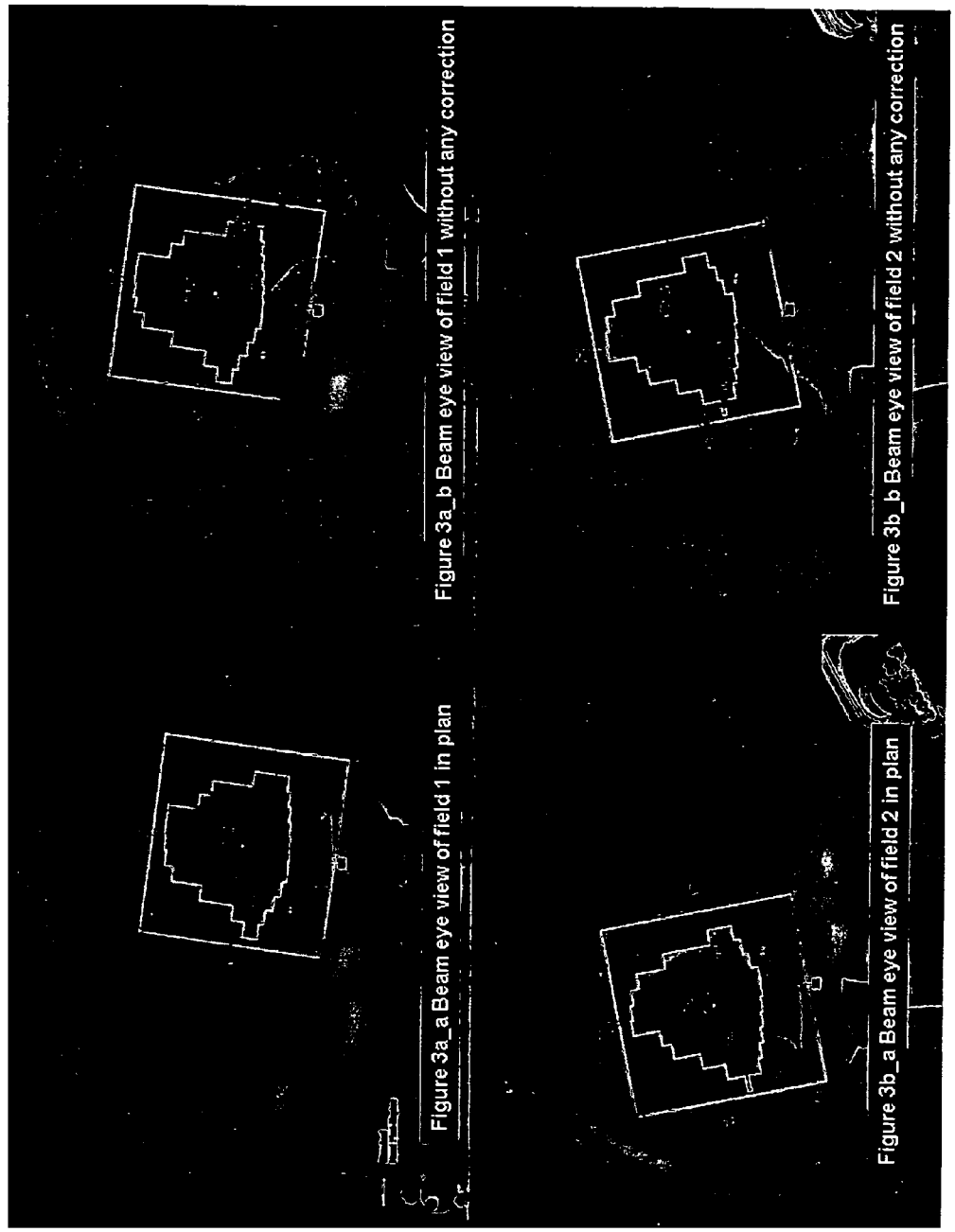

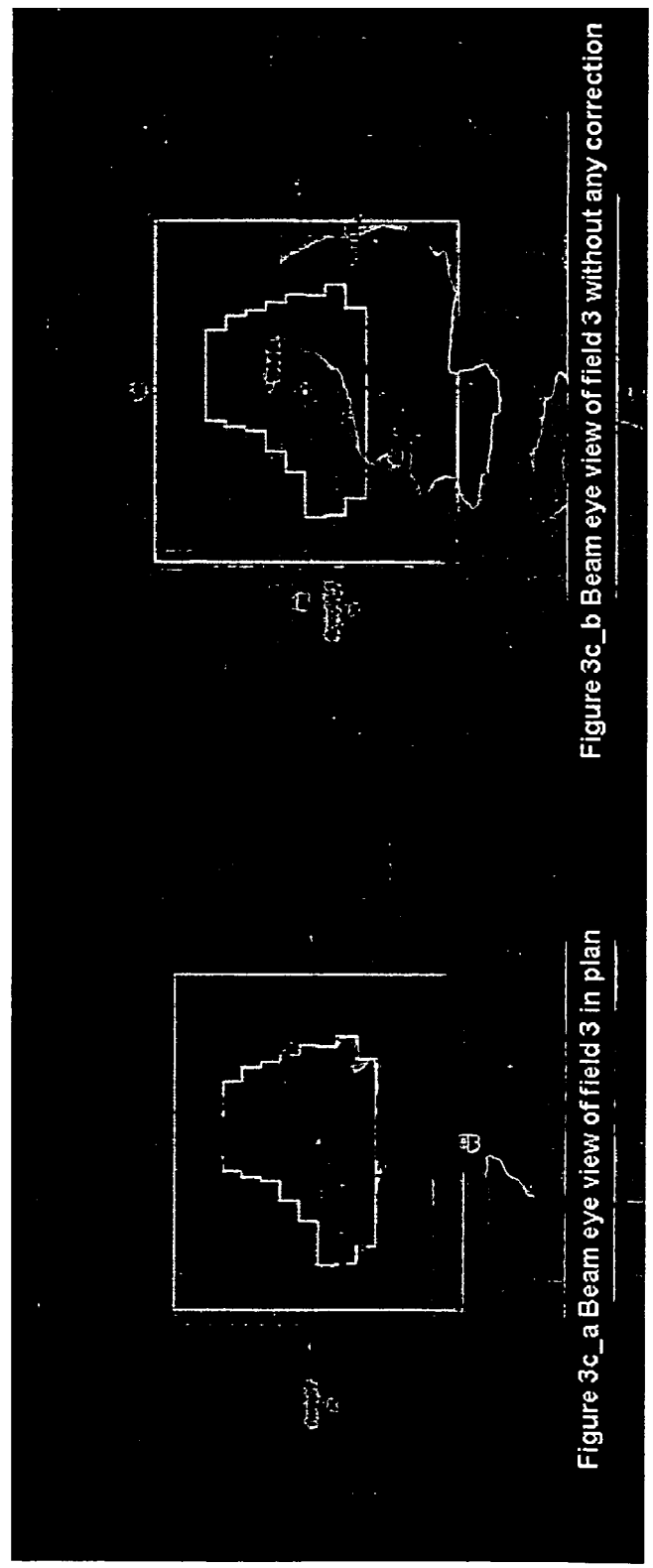

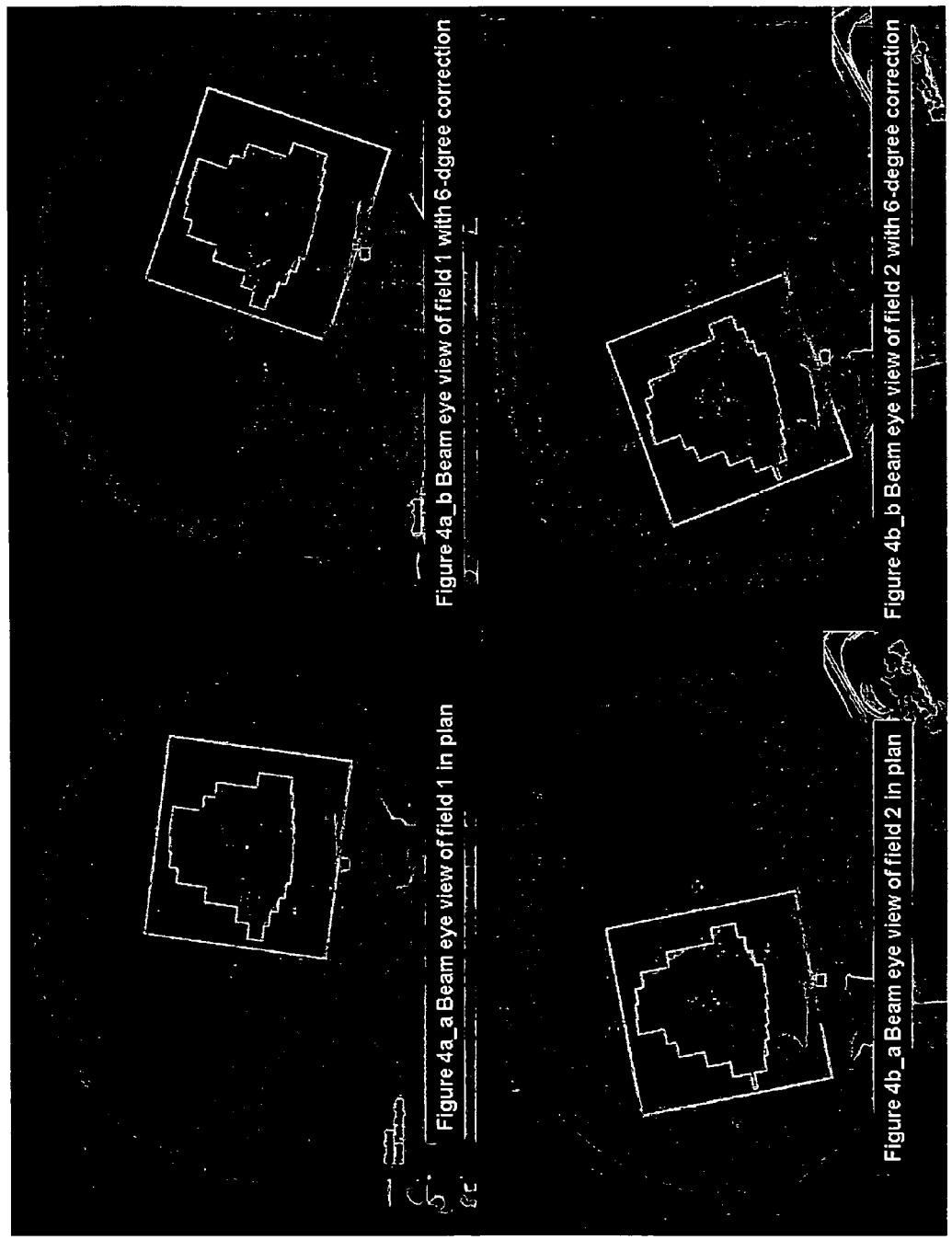

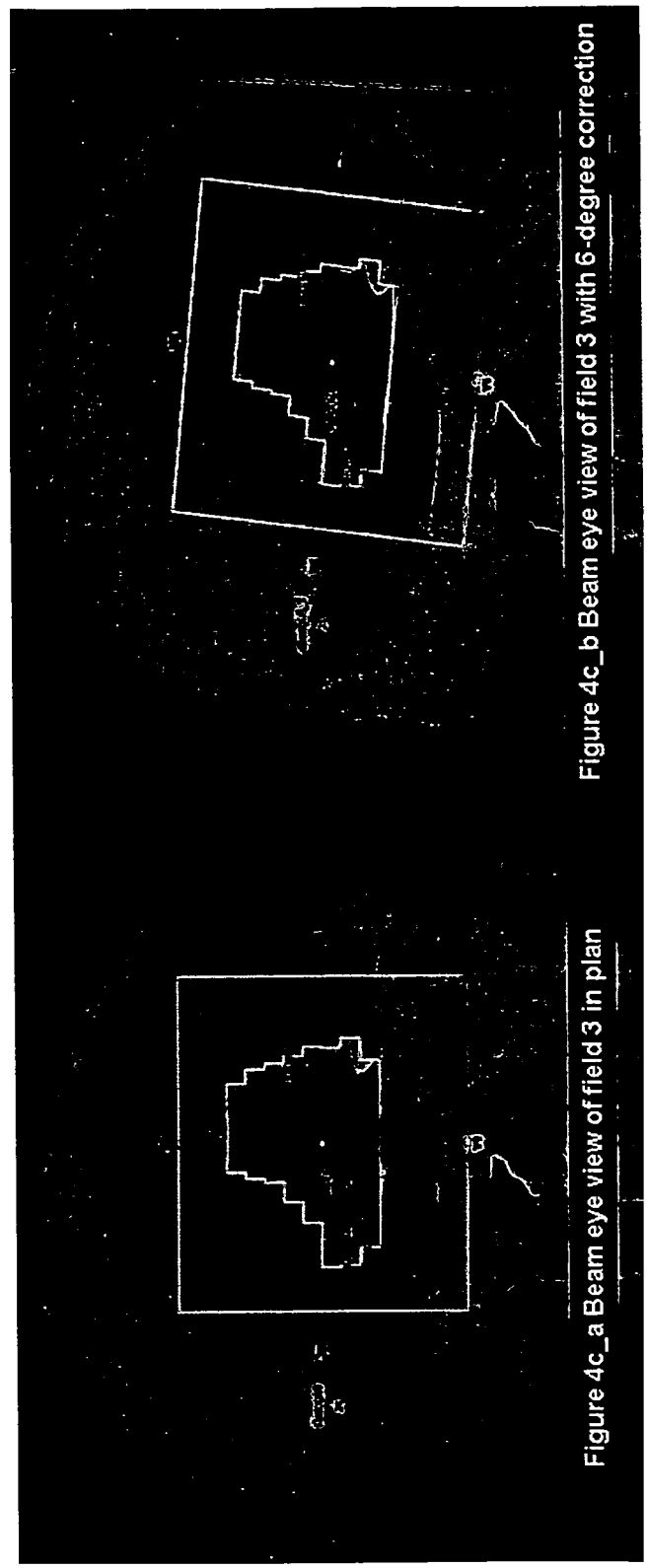

METHOD TO IMPLEMENT FULL SIX-DEGREE TARGET SHIFT CORRECTIONS IN RADIOTHERAPY

FIELD OF THE INVENTION

The present invention relates to a method to correct errors introduced by movement of the targeted area of radiation beams, and in particular to a method using transformation matrices to correct for image target movements from planned target locations used in image guided radiotherapy.

BACKGROUND OF THE INVENTION

Generally, the present invention relates to radiotherapy and more particularly to a procedure that creates a three dimensional picture of a location or area in the body of a patient to be treated, such as a tumor. Radiotherapy generally involves the use of an external beam with a linear accelerator, which largely delivers photons (γ-radiation). Neutron beam radiotherapy is used for some tumors with a narrow tissue margin. Electron beam radiotherapy has a very short tissue penetration and is typically used for skin or superficial cancers. Proton therapy can provide very narrow depth of field exposure with sharp margins.

Typically the patient undergoes a CT (Computerised Tomography) scan of the location to undergo treatment in a proposed treatment position. The images from this scan are transferred to a computer to plan the patient treatment, and the physician traces the outline of the tumor and normal organs on each slice of the CT scan. The treatment planning computer allows the physician to try different beam arrangements on the patient, a process sometimes referred to as virtual simulation. The treatment planning computer may show the beam's eye view (BEV), which is a visual depiction of the treatment field in relation to the tumor and the bony anatomy of the patient as well as normal organs. Using information from the BEV, physicians can design custom blocking of parts of the radiation beam in order to protect normal tissue as much as possible. This allows doctors to provide the highest possible dose of radiation to the tumor.

One form of radiotherapeutic treatment is known as Intensity-Modulated Radiation Therapy (IMRT) which utilize machines that are a specialized case of three dimensional conformal therapy that allow for the modulation of certain intensities associated with a specific beam-angle configuration such that any radiosensitive organs that the beam passes through are subjected to a diminished dose. Another treatment is known as Image Guided Radiation Therapy (IGRT) where the electron beam machines have a CT scanner integrated with the treatment system, or an X-Ray Tube and a Si-detector mounted on the gantry of the linear accelerator. The patient can be scanned and the tumor located in three dimensional space immediately before treatment. The ability to correct for movement and setup errors allows smaller margins to be used, protective healthy tissue and escalating the tumor dose.

Most of the new equipment used in radiotherapy have the ability to provide very precise adjustment to the orientation of the beams produced and the target to be treated. Most of the adjustment/aligning techniques use computerization to control finite variation in the x, y, and z axes. Such adjustments control the rotational and planar alignment, for example, of the gantry section of the radiation equipment and or the treatment couch on which the patient is located. The advances that have occurred in radiotherapy technology permit the use of volumetrically acquired anatomic information to plan a course of radiation therapy. Beams can be shaped according to the projection of the target along the beam's axis with appropriate adjustments for anatomic routes of tumor spread and anatomic barriers to tumor spread. This three dimensional conformal radiation therapy (3DCRT) can decrease normal tissue toxicity through shielding otherwise unshielded normal tissues. A further extrapolation of 3DCRT and the use of computer technology to determine beam apertures and fluences is intensity modulated radiotherapy (IMRT), which has also been used to conformally deliver radiation doses to the planned target volume. IMRT can further reduce radiation doses to the normal tissues surrounding a target. This increase in the ratio of the dose given to the target relative to the dose given to normal tissues can reduce normal tissue radiotherapy toxicity. This increased ratio of dose in the target as compared to the normal tissues also allows increased radiation doses to the target, while maintaining the same dose to the adjacent normal tissues to achieve better tumor control with the same level of normal tissue toxicity. All of these adjustments are designed to assure that the actual treatment with the beams precisely follows the plan for the treatment prepared by the physicians and technologists. However, treatment position setup errors often introduce variations in the position of the treatment target relative to the planned radiation beams. These errors can also be introduced by the movement of a target relative to setup marks or to other relevant landmarks that are used to position a patient for radiotherapy. Such variations can cause dose deviations from the planned doses and result in sub-optimal treatments where the entire target is not irradiated or a critical structure receives more than the desired radiation doses. Clinically available technology for image guided radiotherapy can detect variations of target position. For example, a number of image guided radiotherapy techniques have various attributes and shortcomings. These techniques include ultrasound systems, an array of infrared-reflecting surface markers, electronic portal imaging systems using bony landmarks or implanted radio-opaque markers as aids to visualization, kV imaging systems registered to the machine isocenter, and in-room CT systems.

Several specially designed IGRT radiotherapy delivery systems (e.g., Cyberknife, Novalis system, and the like) have been introduced and utilized to address the target motion and shift problems. For most of linear accelerator based treatment machines, target shift corrections are mainly achieved geometrically by moving the treatment couch with appropriate amounts of translational motion, namely, in the vertical, longitudinal and lateral directions together with rotation of the treatment couch. However, in reality, a more accurate correction of the target shift involves not only the three translational movements, but also three rotational movements. However, almost all treatment couches in clinical use can only rotate in one direction, so that a complete and accurate correction of a target shift cannot currently be achieved by couch movements alone.

Notwithstanding the advent of these recent systems there is great need to provide a method for readily correcting positioning error to assure the precisely planned treatment dose and topology is provided to the patient.

Accordingly, it is an object of the present invention to provide a means for quickly and accurately correcting for a deviation of the treatment procedure and the planned procedure. It is a further object of the present invention to provide a number of transformations matrices that will permit rapid deployment into the computer control systems of clinical radiation facilities.

SUMMARY OF THE INVENTION

Generally, the methods of the present invention provide transformations that facilitate the correction of target position variations between a patient's planned treatment and the actual treatment positions at the time of treatment and restore the original beam geometries relative to the patient's planned treatment. The invention utilizes three matrix transformations: 1) transformation of beams from the machine coordinate system to the patient coordinate system as provided in a patient geometry in the approved dosimetric plan; 2) transformation of beams from the patient coordinate system in the approved radiotherapy plan to the patient coordinate system that is identified at the time of treatment; and 3) transformation of beams from the patient coordinate system at the time of treatment in the treatment patient geometry back to the machine coordinate system. In the present invention it is preferable that the transformation matrix used for the second transformation is determined through the use of image-guided radiotherapy technology. Use of the image-guided radiotherapy facilitates correction. However, other methods are available such as the fixed point, described hereinafter, but which are slower.

By using these matrix transformations, the isocenter coordinates, the gantry, couch and collimator angles of the beams for the treatment, adjusted for any shift in the location of the target can be derived. Utilizing the transforms, new beam parameters can be determined that will possess the same positions and orientations relative to the patient target as provided in the treatment plan. This is generally achieved by adjusting the patient treatment couch, and setting the beams in the newly derived gantry, collimator, and couch angles, so that any changes in the patient target location that occur between the time of the plan and the time of treatment can be fully corrected.

Other advantages of the present invention will become apparent from a perusal of the following detailed description of the presently preferred embodiments and the accompanying figures set forth below.

BRIEF DESCRIPTION OF THE DRAWINGS

FIG. 3 shows a comparison of beam portals on DRRs between the planned beams and the setup treatment beams that were not corrected for target shift in a clinical case.

FIG. 3a_a: beam portal of planned field 1;
FIG. 3a_b: beam portal of the setup treatment field 1;
FIG. 3b_a: beam portal of planned field 2;
FIG. 3b_b: beam portal of the setup treatment field 2;
FIG. 3c_a: beam portal of planned field 3;
FIG. 3c_b: beam portal of the setup treatment field 3.

FIG. 4 shows a comparison of beam portals on DRRs between the planned beams and the beams that were corrected for the target shift in the clinical case shown in FIG. 3.

FIG. 4a_a: beam portal of planned field 1;
FIG. 4a_b: beam portal of the corrected treatment field 1;
FIG. 4b_a: beam portal of planned field 2;
FIG. 4b_b: beam portal of the corrected treatment field 2;
FIG. 4c_a: beam portal of planned field 3;
FIG. 4c_b: beam portal of the corrected treatment field 3.

PRESENTLY PREFERRED EMBODIMENT

Specifically, the present invention utilizes three matrix transformations, namely:

1) transformation of beams from the machine coordinate system to the patient coordinate system as provided in a patient geometry in the approved dosimetric plan;

2) transformation of beams from the patient coordinate system in the approved radiotherapy plan to the patient coordinate system that is identified at the time of treatment; and 3) transformation of beams from the patient coordinate system at the time of treatment in the treatment patient geometry back to the machine coordinate system.

Utilizing the method and transformation matrices of the present invention a complete and accurate correction of target shift can be implemented by not only moving the treatment couch but also changing the beam gantry and collimator angles. With the method and the matrices set forth below, new isocenter coordinates, gantry, collimator and table angles of the beams in patient treatment can be derived. The derived beam parameters in accordance with the invention will provide the treatment beams with the same target positions and orientations relative to the target as calculated for the patient treatment plan.

To accurately correct any target shifts, it is necessary to derive the beam parameters (isocenter coordinates, gantry, collimator and table angles) required at the time of treatment so that the beams to be used in a given treatment and the beams approved in the plan possess the same relative geometric relationships to a patient's anatomy. In the present invention, it preferable to use image guidance as it is generally known within the radiotherapy treatment environment. With image guided radiotherapy, target shifts can be detected, and the transformation matrix between the treatment patient geometry and the plan patient geometry can be derived.

In a presently preferred embodiment of the invention, three coordinate systems are used to make the corrections. The coordinate systems preferably used and the beam parameters (those of the gantry, collimator, and couch) include:

a. Machine Coordinate System (Hereinafter "Room Coordinate System").

Figure 1A:
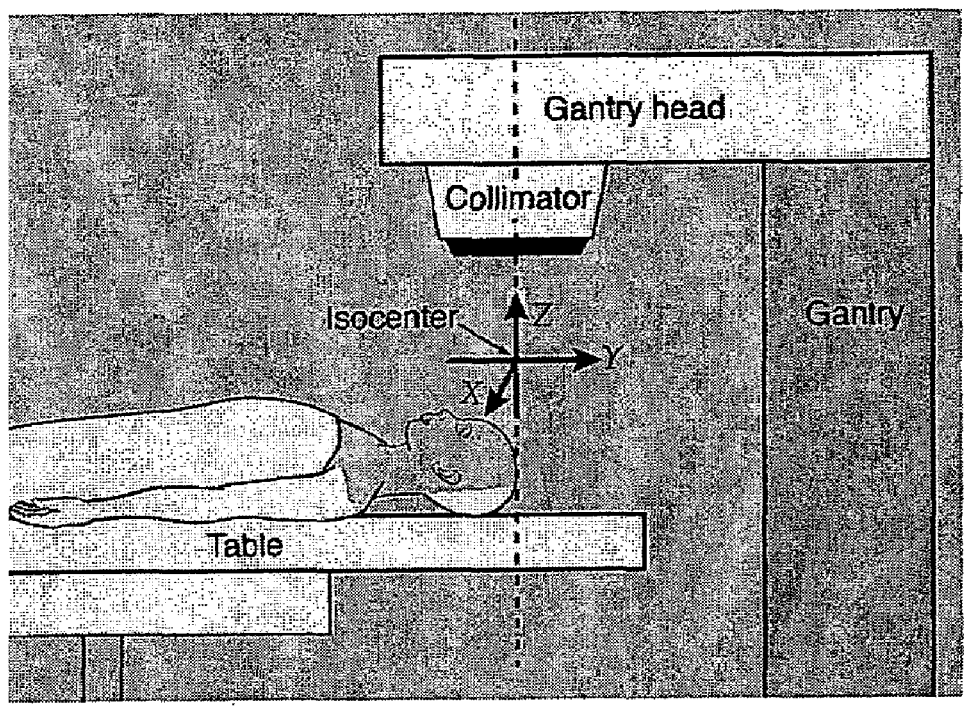
FIGS. 1a and 1b depict the coordinate system for the machine and the patient.

Referring to FIG. 1a, the machine coordinate system has its origin at the machine isocenter; the positive x-axis direction is from left to right when facing the machine gantry; the positive y-axis direction is toward the linear accelerator; and the positive z-axis direction is from the floor to the ceiling. The machine coordinate system is fixed in the space occupied by the treatment room and does not move with the machine.

b. Plan Patient Coordinate System.

Figure 1B:
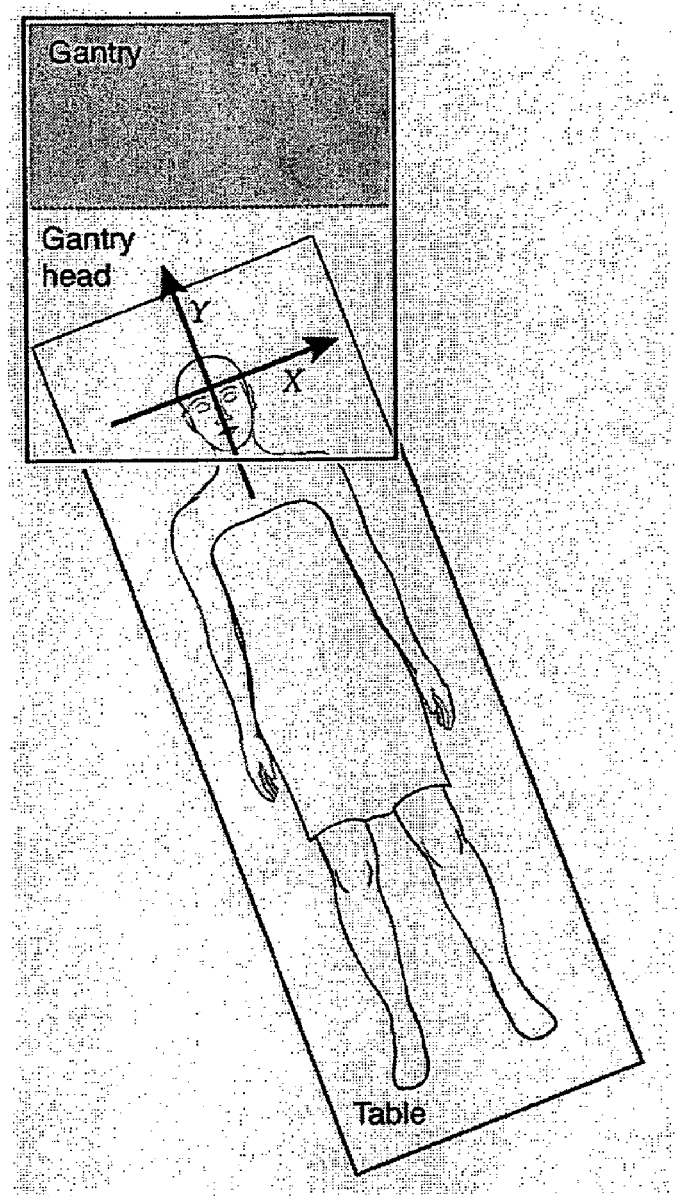

The planned patient coordinate system is fixed with regards to the patient anatomy in the plan patient geometry as defined by the CT images obtained for the treatment planning. Referring to FIG. 1b, with the patient is in the supine position and looking from the distal end of the couch, the positive x-axis direction is from the right of the patient to the left, the positive y-axis direction is from patient caudad to craniad (FIG. 1b), and the positive z-axis direction is from patient posterior to anterior (not shown in FIG. 1b). In this embodiment the treatment isocenter is selected as the origin to coincide with the machine isocenter.

c. Treatment Patient Coordinate System.

The treatment patient coordinate system also is fixed with respect to the patient anatomy at the time of imaging within the treatment environment. The x, y, and z axes are oriented just as in the plan patient coordinate system, with the positive x-axis direction from patient right to left, positive y-axis direction from patient feet to head, and positive z-axis direction from patient posterior to anterior (FIG. 1b). The treatment isocenter is also selected as the origin in the treatment patient coordinate system to coincide with the machine isocenter.

While the plan patient coordinate system and the treatment patient coordinate system are shown in this embodiment to be identical, their relative geometric relationships to the patient's anatomy typically are not generally same since the patient's position on the couch may differ between the plan and actual treatment. On the other hand, during the patient plan imaging and treatment, a patient is assumed to be stationary relative to the machines' table tops and the patient coordinate systems are fixed relative to patient anatomy, the two patient coordinate systems can only translate and rotate relative to the room coordinate system by movement of the couch about its axes.

Figure 2A:
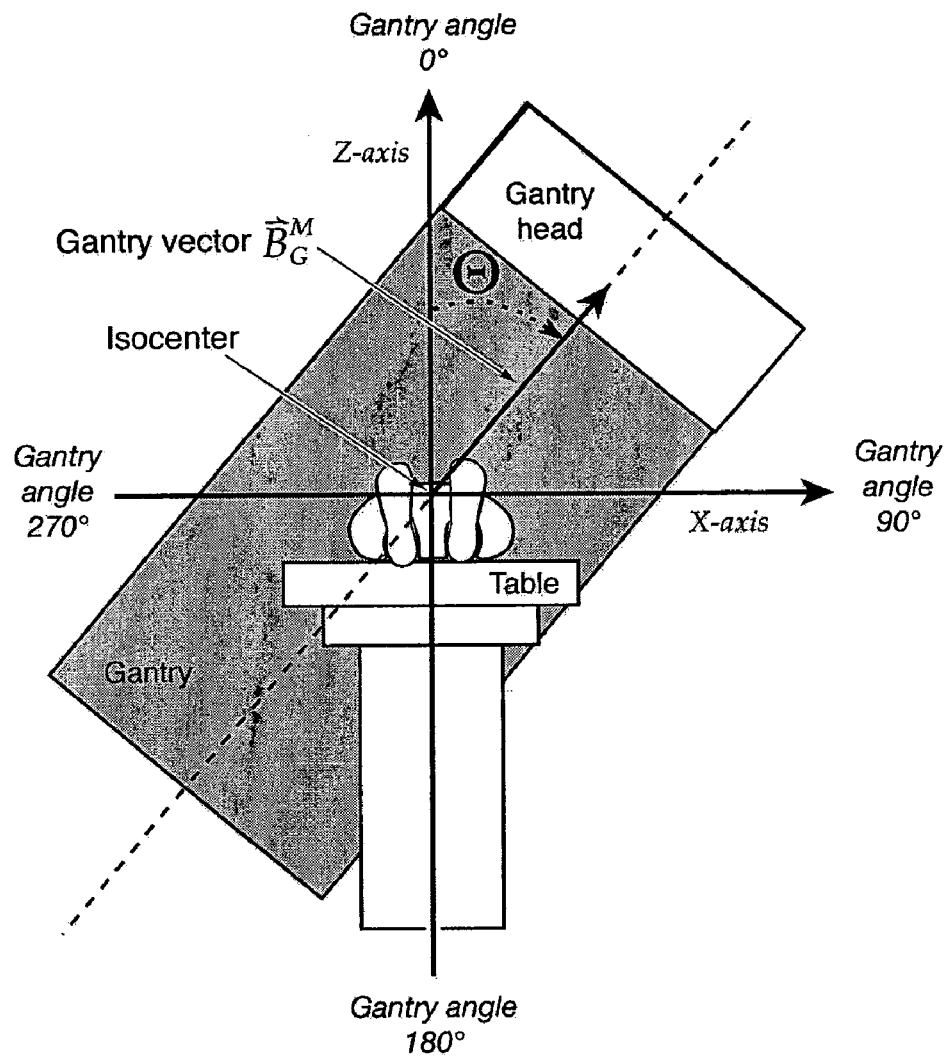
FIGS. 2a, 2b and 2c graphically define the gantry vector $\vec{B}_G^M$, collimator vector $\vec{B}_C^M$, and table vector $\vec{B}_T^M$.
Figure 2B:
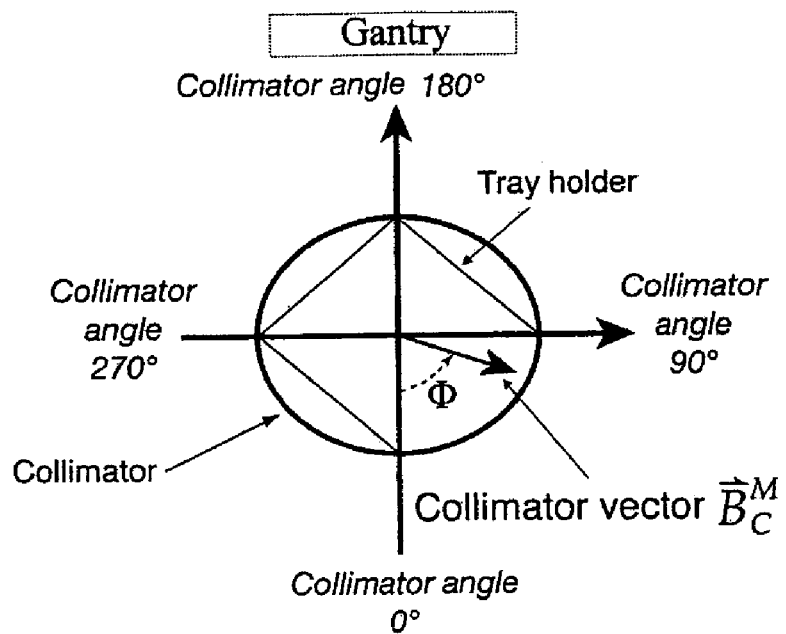
Figure 2C:
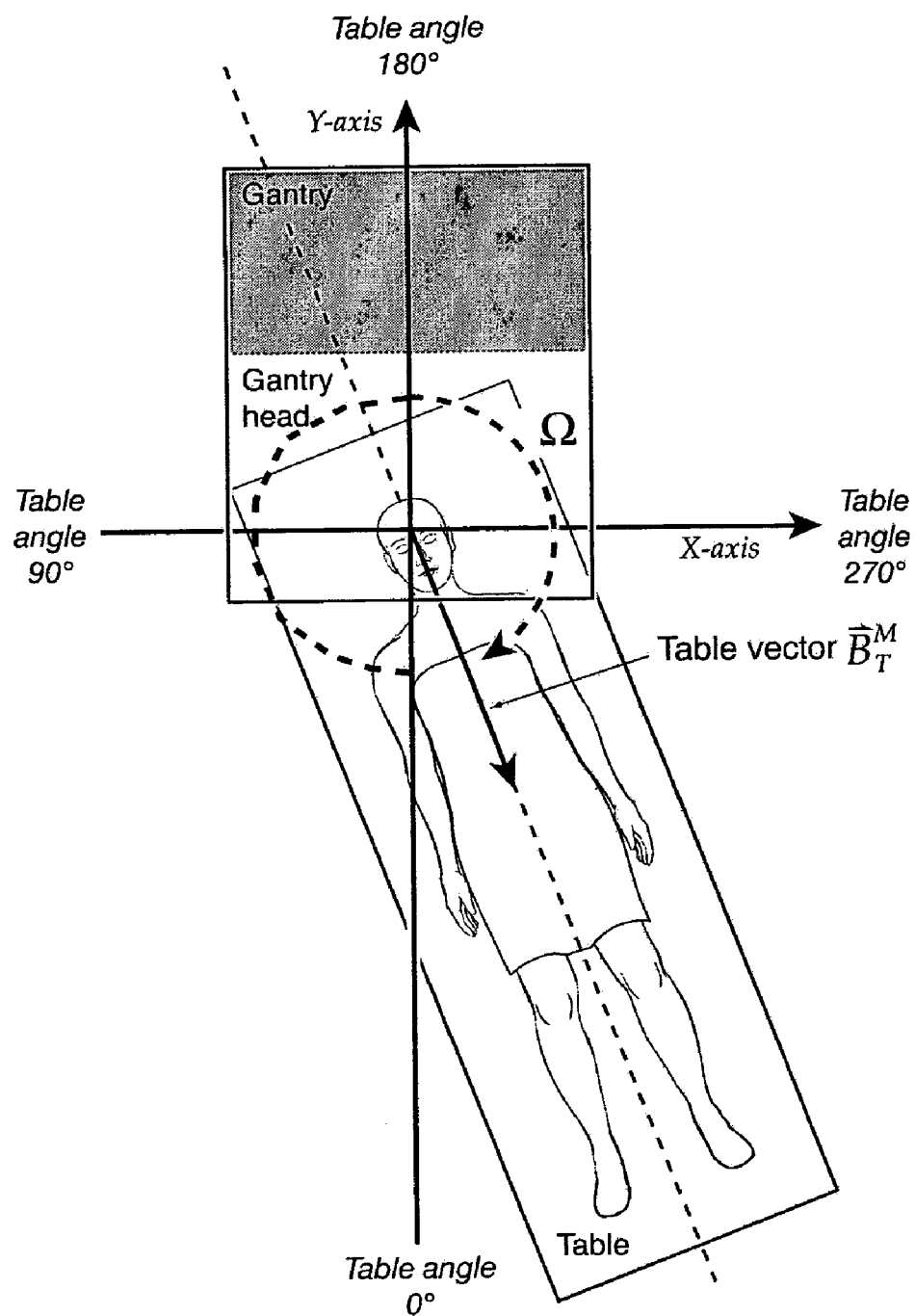

Referring to FIGS. 2a–2c, three vectors describe the positions of gantry, collimator of a beam, and table angular position. The gantry position: unit vector $\vec{B}_G^M$ pointing from the machine isocenter to the machine gantry head along the beam central axis (FIG. 2a) and is only in the x-z plane of the room coordinate system since a linear accelerator's gantry only rotate in that plane. The collimator position: unit vector $\vec{B}_C^M$ pointing from the center of collimator to the open side of the tray at the level of the collimator as shown in FIG. 2b. This vector is perpendicular to the beam central axis and moves with both gantry rotation and collimator rotation. The couch or table angular position: unit vector $\vec{B}_T^M$ pointing from the machine isocenter to the distal end and parallel to the longitudinal axis of the table as shown in FIG. 2c. The table vector only rotates in the x-y plane of the room coordinate system.

Based on the IEC coordinate system conventions used for linear accelerators (FIG. 2), the machine coordinate system, the gantry vector $\vec{B}_G^M$, the collimator vector $\vec{B}_C^M$, and the table vector $\vec{B}_T^M$, are represented as follows:

$$\vec{B}_G^M = \begin{pmatrix} \sin\Theta \\ 0 \\ \cos\Theta \end{pmatrix}, \vec{B}_C^M = \begin{pmatrix} \cos\Theta \sin\Phi \\ -\cos\Phi \\ -\sin\Theta \sin\Phi \end{pmatrix}, \vec{B}_T^M = \begin{pmatrix} -\sin\Omega \\ -\cos\Omega \\ 0 \end{pmatrix} \quad (1)$$

where $\Theta$, $\Phi$, $\Omega$ are the gantry, collimator, and table angles, respectively, and B, G, C, T, and M are the letters used to represent Beam, Gantry, Collimator, Table and rooM (or Machine), respectively.

In the presently preferred embodiment, the transformation matrix between the plan and the treatment patient coordinate systems is determined by using image guided radiotherapy technologies such as in-room CT or orthogonal x-ray images where the target can be located within the patient by definite radiographic characteristics. Where a target can be clearly defined, ultrasonographic imaging can be used when the patient is positioned for treatment. With image guided radiotherapy technology, patient anatomy images in the treatment environment can be obtained for positioning verification immediately prior to treatment. Such verification images can be either registered to the images from the treatment planning study or can be quantified a transformation matrix between the plan and treatment patient geometry can be derived during the image registration process. Target shift also can be detected by placement of small opaque markers in the soft-tissue tumor using the identification markers in the plan and treatment verification images. Using the corresponding markers, the transformation matrix between the plan and treatment patient geometry can be established.

The following transformation matrices define a preferred method for correcting target shift between the coordinates of the planned treatment and actual treatment. In this embodiment a translational matrix and a rotational matrix are used. Further, this embodiment considers only one beam but can be used for multiple beams.

a. Transformation Matrices Between the Room Coordinate System and the Plan Patient Coordinate System.

A point is expressed as $$\vec{r}^M = \begin{pmatrix} x^M \\ y^M \\ z^M \end{pmatrix}$$

in the room coordinate system, and as $$\vec{r}^P = \begin{pmatrix} x^P \\ y^P \\ z^P \end{pmatrix}$$

in the plan patient coordinate system within the approved dosimetric plan, such that $$\begin{pmatrix} x^P \\ y^P \\ z^P \end{pmatrix} = \begin{pmatrix} x^{P \leftarrow M} \\ y^{P \leftarrow M} \\ z^{P \leftarrow M} \end{pmatrix} + T^{P \leftarrow M} \otimes \begin{pmatrix} x^M \\ y^M \\ z^M \end{pmatrix}, \quad (2)$$

where $$\begin{pmatrix} x^{P \leftarrow M} \\ y^{P \leftarrow M} \\ z^{P \leftarrow M} \end{pmatrix}$$

are the coordinates of the origin of the room coordinate system in the plan patient coordinate system established in the geometry of the approved patient dosimetric plan, and $$T^{P \leftarrow M} = \begin{pmatrix} \cos \Omega^P & -\sin \Omega^P & 0 \\ \sin \Omega^P & \cos \Omega^P & 0 \\ 0 & 0 & 1 \end{pmatrix} \quad (3)$$

is the rotational transformation matrix from the room coordinate system to the plan patient coordinate system in the plan patient geometry when the table angle in the plan is $\Omega^P$. The rotational transformation matrix is straight forward because the treatment couch can only rotate in the x-y plane and the patient is assumed not to move. By defining the machine isocenter the same as the treatment isocenter and thus the origin for both the room coordinate system and the plan patient coordinate system, then $$\begin{pmatrix} x^{P \leftarrow M} \\ y^{P \leftarrow M} \\ z^{P \leftarrow M} \end{pmatrix} = \begin{pmatrix} 0 \\ 0 \\ 0 \end{pmatrix}$$

and Equation 2 becomes $$\begin{pmatrix} x^P \\ y^P \\ z^P \end{pmatrix} = T^{P \leftarrow M} \otimes \begin{pmatrix} x^M \\ y^M \\ z^M \end{pmatrix}.$$

b. Transformation Matrix to Register Patient Anatomies Between the Plan Patient Coordinate System and the Treatment Patient Coordinate System The transformation matrix to register patient anatomies between the plan and the treatment patient coordinate systems is the one that relates the coordinates of a same anatomy point in the two coordinate systems. Assuming a point is expressed as $$\vec{r}^P = \begin{pmatrix} x^P \\ y^P \\ z^P \end{pmatrix}$$

in the plan patient coordinate system, and as $$\vec{r}^T = \begin{pmatrix} x^T \\ y^T \\ z^T \end{pmatrix}$$

in the patient coordinate system imaged in the treatment environment, then $$\begin{pmatrix} x^T \\ y^T \\ z^T \end{pmatrix} = \begin{pmatrix} x^{T \leftarrow P} \\ y^{T \leftarrow P} \\ z^{T \leftarrow P} \end{pmatrix} + T^{T \leftarrow P} \otimes \begin{pmatrix} x^P \\ y^P \\ z^P \end{pmatrix}, \quad (4)$$

where $$\begin{pmatrix} x^{T \leftarrow P} \\ y^{T \leftarrow P} \\ z^{T \leftarrow P} \end{pmatrix}$$

is a translational vector, and $T^{T \leftarrow P}$ is a rotational matrix and can be expressed as $$T_{T \leftarrow P} = T_x^{T \leftarrow P} T_y^{T \leftarrow P} T_z^{T \leftarrow P} \quad (5).$$

$$T_x^{T \leftarrow P} = \begin{pmatrix} 1 & 0 & 0 \\ 0 & \cos\theta_x & -\sin\theta_x \\ 0 & \sin\theta_x & \cos\theta_x \end{pmatrix}, T_y^{T \leftarrow P} = \begin{pmatrix} \cos\theta_y & 0 & \sin\theta_y \\ 0 & 1 & 0 \\ -\sin\theta_y & 0 & \cos\theta_y \end{pmatrix}, \quad (6)$$

$$\text{and } T_z^{T \leftarrow P} = \begin{pmatrix} \cos\theta_z & -\sin\theta_z & 0 \\ \sin\theta_z & \cos\theta_z & 0 \\ 0 & 0 & 1 \end{pmatrix}$$

are three individual rotational matrices and angles $\theta_x$, $\theta_y$ and $\theta_z$ are the angles with which the plan patient coordinate system rotated around the x, y and z axes of the treatment patient coordinate system, respectively. The sequence of the transformations is not interchangeable. Once the three angles are determined, the rotational matrix $T^{T \leftarrow P}$ is derived from Equations 5 and 6.

The solution of matrices $$\begin{pmatrix} x^{T \leftarrow P} \\ y^{T \leftarrow P} \\ z^{T \leftarrow P} \end{pmatrix}$$

and $T^{T \leftarrow P}$ is preferably achieved by direct output from software capable of automated image registration. Alternatively, it is derived from by the identification of three (or more) non co-linear fixed points in the treatment area.

In the preferred method, there are registration algorithms that are available for the alignment of patient anatomy between the image set obtained for treatment planning and the image set obtained in the treatment environment which use rigid body translations along and rotation around the three orthogonal axes. Thus, if the corresponding coordinate systems used in the image registration are the same as the patient coordinate systems in the plan and the treatment patient geometries, the resultant translation and rotation outputs from the image registration software are the transformation matrices from the patient coordinate system in the plan patient geometry to that in the treatment patient geometry. However if they are not the same or unknown, then fixed-points based method can be used as an alternative way to derive these transformation matrices.

To use the fixed-points based method, it is necessary to identify at least three corresponding non co-linear points from the two different image sets. Radioopaque markers placed in a soft tissue tumor (target) as an aid to visualization, can be used to derive the transformation matrices. However, markers that do not maintain a fixed relation to the target normally will not provide accurate transformations. Using three fixed non co-linear points identified on both the image set in the plan image set (patient geometry) and the treatment verification image set (patient geometry), the three fixed points on the image set in the plan is identified, digitized and expressed as $$\vec{r}_1^P = \begin{pmatrix} x_1^P \\ y_1^P \\ z_1^P \end{pmatrix}, \quad \vec{r}_2^P = \begin{pmatrix} x_2^P \\ y_2^P \\ z_2^P \end{pmatrix}, \quad \text{and} \quad \vec{r}_3^P = \begin{pmatrix} x_3^P \\ y_3^P \\ z_3^P \end{pmatrix}$$

in the plan patient coordinate system; and on the treatment verification image set as, $$\vec{r}_1^T = \begin{pmatrix} x_1^T \\ y_1^T \\ z_1^T \end{pmatrix}, \quad \vec{r}_2^T = \begin{pmatrix} x_2^T \\ y_2^T \\ z_2^T \end{pmatrix}, \quad \text{and} \quad \vec{r}_3^T = \begin{pmatrix} x_3^T \\ y_3^T \\ z_3^T \end{pmatrix}$$

in the treatment patient coordinate system. The two sets of coordinates are related with equation group $$\begin{pmatrix} x_1^T \\ y_1^T \\ z_1^T \end{pmatrix} = \begin{pmatrix} x^{T \leftarrow P} \\ y^{T \leftarrow P} \\ z^{T \leftarrow P} \end{pmatrix} + T^{T \leftarrow P} \otimes \begin{pmatrix} x_1^P \\ y_1^P \\ z_1^P \end{pmatrix}, \quad (7)$$

$$\begin{pmatrix} x_2^T \\ y_2^T \\ z_2^T \end{pmatrix} = \begin{pmatrix} x^{T \leftarrow P} \\ y^{T \leftarrow P} \\ z^{T \leftarrow P} \end{pmatrix} + T^{T \leftarrow P} \otimes \begin{pmatrix} x_2^P \\ y_2^P \\ z_2^P \end{pmatrix},$$

$$\begin{pmatrix} x_3^T \\ y_3^T \\ z_3^T \end{pmatrix} = \begin{pmatrix} x^{T \leftarrow P} \\ y^{T \leftarrow P} \\ z^{T \leftarrow P} \end{pmatrix} + T^{T \leftarrow P} \otimes \begin{pmatrix} x_3^P \\ y_3^P \\ z_3^P \end{pmatrix},$$

where $$\begin{pmatrix} x_{p \rightarrow t} \\ y_{p \rightarrow t} \\ z_{p \rightarrow t} \end{pmatrix} = \vec{\delta}_{p \rightarrow t}$$

are the coordinates of the origin (the isocenter, as defined) from the approved dosimetric plan within the geometry of the patient at the time of treatment. $T^{T \leftarrow P}$ is a rotational transformation matrix between the plan patient coordinate systems and the treatment patient coordinate systems which is formed with three separate rotational transformations around the three orthogonal axes within the treatment patient coordinate system that has been defined in the patient imaging acquired in the treatment environment. Since $$\begin{pmatrix} x_i^P \\ y_i^P \\ z_i^P \end{pmatrix} \text{ and } \begin{pmatrix} x_i^T \\ y_i^T \\ z_i^T \end{pmatrix}$$

(i=1, 2, 3) are known, from Equations 6 and 7, $$\begin{pmatrix} x^{T \leftarrow P} \\ y^{T \leftarrow P} \\ z^{T \leftarrow P} \end{pmatrix},$$

$\theta_x$, $\theta_y$ and $\theta_z$ (essentially $T^{T \leftarrow P}$) can be derived.

c. Transformation Matrices Between the Treatment Patient Coordinate System and the Room Coordinate System.

A point expressed as $$\vec{r}^T = \begin{pmatrix} x^T \\ y^T \\ z^T \end{pmatrix}$$

in the treatment patient coordinate system, and as $$\vec{r}^M = \begin{pmatrix} x^M \\ y^M \\ z^M \end{pmatrix}$$

in the room coordinate system, provides $$\begin{pmatrix} x^M \\ y^M \\ z^M \end{pmatrix} = \begin{pmatrix} x^{M \leftarrow T} \\ y^{M \leftarrow T} \\ z^{M \leftarrow T} \end{pmatrix} + T^{M \leftarrow T} \otimes \begin{pmatrix} x^T \\ y^T \\ z^T \end{pmatrix} \quad (8)$$

where $$\begin{pmatrix} x^{M \leftarrow T} \\ y^{M \leftarrow T} \\ z^{M \leftarrow T} \end{pmatrix}$$

are the coordinates of the origin of the treatment patient coordinate system in the room coordinate system, and $$T^{M \leftarrow T} = \begin{pmatrix} \cos\Omega^T & \sin\Omega^T & 0 \\ -\sin\Omega^T & \cos\Omega^T & 0 \\ 0 & 0 & 1 \end{pmatrix} \quad (9)$$

is the rotational transformation matrix from the treatment patient coordinate system to the room coordinate system when the treatment couch angle in the treatment is $\Omega^T$. Further, since the machine isocenter is the origin of both the room and the treatment patient coordinate system, Equation 8 is simplified to $$\begin{pmatrix} x^M \\ y^M \\ z^M \end{pmatrix} = T^{M \leftarrow T} \otimes \begin{pmatrix} x^T \\ y^T \\ z^T \end{pmatrix}.$$

In the following example only one beam is considered.

A. Establishment of Plan Beam Isocenter in the Treatment Patient Coordinate System As defined, the coordinate of the isocenter of the beam is $$\vec{r}_{iso}^M = \begin{pmatrix} 0 \\ 0 \\ 0 \end{pmatrix}$$

in the room coordinate system in the plan. Based on Equations 2 and 4, in the treatment patient coordinate system, the coordinate of the isocenter of the beam as defined in the plan become $$\begin{pmatrix} x_{iso}^T \\ y_{iso}^T \\ z_{iso}^T \end{pmatrix} = \begin{pmatrix} x^{T \leftarrow P} \\ y^{T \leftarrow P} \\ z^{T \leftarrow P} \end{pmatrix} + T^{T \leftarrow P} \otimes \left\{ \begin{pmatrix} x^{P \leftarrow M} \\ y^{P \leftarrow M} \\ z^{P \leftarrow M} \end{pmatrix} + T^{P \leftarrow M} \otimes \begin{pmatrix} 0 \\ 0 \\ 0 \end{pmatrix} \right\} \quad (10)$$

$$= \begin{pmatrix} x^{T \leftarrow P} \\ y^{T \leftarrow P} \\ z^{T \leftarrow P} \end{pmatrix} = \vec{\delta}_{iso}$$

since $$\begin{pmatrix} x^{P \leftarrow M} \\ y^{P \leftarrow M} \\ z^{P \leftarrow M} \end{pmatrix} = \begin{pmatrix} 0 \\ 0 \\ 0 \end{pmatrix}$$

as defined. $\vec{\delta}_{iso}$ is isocenter shift, which adjustment requires longitudinal, lateral, and vertical movements of treatment couch.

b Establishment of Plan Beam Gantry Angle, Couch Angle, and Collimator Angle in the Treatment Environment To fully correct the target shift, the gantry angle, collimator angle, and couch angle of the beam in the plan are established such that the beam is in the same geometric orientation relative to the patient anatomy at the time of treatment as generated and approved for the plan that are based on the treatment planning CT. $\vec{B}_{G,p}^M$, $\vec{B}_{C,p}^M$ and $\vec{B}_{T,p}^M$ represent the gantry, collimator, and table angular positions respectively in the room coordinate system as in the plan, thus $$\vec{B}_{G,p}^M = \begin{pmatrix} \sin\Theta_p \\ 0 \\ \cos\Theta_p \end{pmatrix}, \quad \vec{B}_{C,p}^M = \begin{pmatrix} \cos\Theta_p \sin\Phi_p \\ -\cos\Phi_p \\ -\sin\Theta_p \sin\Phi_p \end{pmatrix}, \quad (11)$$

$$\vec{B}_{T,p}^M = \begin{pmatrix} -\sin\Omega_p \\ -\cos\Omega_p \\ 0 \end{pmatrix}$$

where $\Theta_p$, $\Phi_p$ and $\Omega_p$ are the beam gantry, collimator and the couch angles in the plan. The beam parameters in the machine coordinate system in the treatment situation are thus $$\vec{B}_{G,t}^M = T^{M \leftarrow T} T^{T \leftarrow P} T^{P \leftarrow M} \vec{B}_{G,p}^M$$

$$\vec{B}_{C,t}^M = T^{M \leftarrow T} T^{T \leftarrow P} T^{P \leftarrow M} \vec{B}_{C,p}^M \quad (12)$$

From Equations 3, 9, 11 and 12, $$\vec{B}_{G,t}^M = \begin{pmatrix} \cos\Omega_t & \sin\Omega_t & 0 \\ -\sin\Omega_t & \cos\Omega_t & 0 \\ 0 & 0 & 1 \end{pmatrix} \otimes T^{T \leftarrow P} \otimes \begin{pmatrix} \cos\Omega_p & -\sin\Omega_p & 0 \\ \sin\Omega_p & \cos\Omega_p & 0 \\ 0 & 0 & 1 \end{pmatrix} \otimes \quad (13)$$

$$\begin{pmatrix} \sin\Theta_p \\ 0 \\ \cos\Theta_p \end{pmatrix}$$

$$= \begin{pmatrix} \cos\Omega_t & \sin\Omega_t & 0 \\ -\sin\Omega_t & \cos\Omega_t & 0 \\ 0 & 0 & 1 \end{pmatrix} \otimes T^{T \leftarrow P} \otimes \begin{pmatrix} \cos\Omega_p \sin\Theta_p \\ \sin\Omega_p \sin\Theta_p \\ \cos\Theta_p \end{pmatrix}$$

$$\vec{B}_{C,t}^M = \begin{pmatrix} \cos\Omega_t & \sin\Omega_t & 0 \\ -\sin\Omega_t & \cos\Omega_t & 0 \\ 0 & 0 & 1 \end{pmatrix} \otimes T^{T \leftarrow P} \otimes \begin{pmatrix} \cos\Omega_p & -\sin\Omega_p & 0 \\ \sin\Omega_p & \cos\Omega_p & 0 \\ 0 & 0 & 1 \end{pmatrix} \otimes$$

$$\begin{pmatrix} \cos\Theta_p \sin\Phi_p \\ -\cos\Phi_p \\ -\sin\Theta_p \sin\Phi_p \end{pmatrix}$$

$$= \begin{pmatrix} \cos\Omega_t & \sin\Omega_t & 0 \\ -\sin\Omega_t & \cos\Omega_t & 0 \\ 0 & 0 & 1 \end{pmatrix} \otimes T^{T \leftarrow P} \otimes$$

$$\begin{pmatrix} \cos\Omega_p \cos\Theta_p \sin\Phi_p + \sin\Omega_p \cos\Phi_p \\ \sin\Omega_p \cos\Theta_p \sin\Phi_p - \cos\Omega_p \cos\Phi_p \\ -\sin\Theta_p \sin\Phi_p \end{pmatrix},$$

where $\Theta_t$, $\Phi_t$ and $\Omega_t$ are the to-be-determined gantry, collimator and couch angles of the beam for the current treatment, with which the beam possesses the same geometric relationships with the patient anatomy as in the plan.

Since the gantry can only rotate in the x-z plane of the room coordinate system, $\vec{B}_{G,t}^M$, has to be parallel to x-z plane of the machine coordinate system. This limitation is overcome by the rotation of the couch, and couch angle $\Omega_t$ is then determined through equations $$\vec{B}_{G,t}{}^M \cdot \vec{j}^M = 0 \quad (14a)$$

Or $$\Omega_t = \arctan\left(\frac{a_{21}\cos\Omega_p\sin\Theta_p + a_{22}\sin\Omega_p\sin\Theta_p + a_{23}\cos\Theta_p}{a_{11}\cos\Omega_p\sin\Theta_p + a_{21}\sin\Omega_p\sin\Theta_p + a_{13}\cos\Theta_p}\right) \quad (14b)$$

if $$T^{T \leftarrow P} = \begin{pmatrix} a_{11} & a_{12} & a_{13} \\ a_{21} & a_{22} & a_{23} \\ a_{31} & a_{32} & a_{33} \end{pmatrix}.$$

The later constraint arises from the fact that when a patient is being treated it is usually the case that the patient head is toward the gantry (feet away from gantry) and under this condition the table angle is between 90 and 270 degree according to accepted conventions, e.g. Medical Systems.

The established gantry angle $\Theta_t$ is determined as:

$$\Theta_t = \begin{cases} \arccos(\vec{B}_{G,t}^M \cdot \vec{k}^M) & \text{if } (\vec{B}_{G,t}^M \times \vec{k}^M) \cdot \vec{j}^M \leq 0 \\ 360 - \arccos(\vec{B}_{G,t}^M \cdot \vec{k}^M) & \text{if } (\vec{B}_{G,t}^M \times \vec{k}^M) \cdot \vec{j}^M > 0, \end{cases} \quad (15)$$

And the collimator angle $\Phi_t$ is determined as:

$$\Phi_t = \begin{cases} 180 - \arccos(\vec{B}_{C,t}^M \cdot \vec{j}^M), & \text{if } (\vec{B}_{C,t}^M \times \vec{j}^M) \cdot \vec{B}_{G,t}^M \geq 0 \\ 180 + \arccos(\vec{B}_{C,t}^M \cdot \vec{j}^M), & \text{if } (\vec{B}_{C,t}^M \times \vec{j}^M) \cdot \vec{B}_{G,t}^M < 0 \end{cases} \quad (16)$$

Once the beam parameters are determined, the planned beam can be re-established in the treatment environment, it will possess the same relative geometric positions with respect to the patient anatomy as in the approved dosimetric plan. This process can be then reiterated for each of the beams used in the treatment.

EXAMPLE

The method of the presently preferred embodiment was utilized in a phantom case. FIGS. 3 and 4 depict the results.

In this example, a brain tumor patient was treated with 3-D conformal radiation therapy. A set of CT scans were acquired before treatment for the purpose of treatment planning. A treatment plan was designed based on the CT scans (using Varian Eclipse™ treatment planning system) and three 6 MV photon beams were used. These three beams are labeled as field 1, field 2, and field 3, respectively. Beam portals of field 1, field 2 and field 3 on the corresponding digitally reconstructed radiographs (DRR) are shown in FIGS. 3a_a, 3b_a, and 3c_a, respectively. Some of the planned beam parameters are also listed in Table 1. A set of CT scans ("treatment" verification CT scan) were acquired using a CT simulator with the patient in the treatment setup position as determined in the treatment plan. A facial mask was used as a fixation device. The three beam portals of field 1, field 2 and field 3, which were set up according to the fiducial markers on the mask and according to the planned beam parameters listed in Table 1, were generated on the corresponding new DRRs that were reconstructed from the acquired CT scans and are shown in FIGS. 3a_b, 3b_b, 3c_b, respectively. It was found from the comparisons between FIG. 3a_a and FIG. 3a_b, FIG. 3b_a and FIG. 3b_b, FIG. 3c_a and FIG. 3c_b that there existed differences between the two sets of beam portals relative to the patient's bony landmarks and structures. This detected shift was most likely due to errors caused by the fixation mask used to set up the patient since organ motion is usually not an issue for brain tumor patients.

To correct for the target shift, the plan CT scans and the "treatment" verification CT scans were registered using a mutual information based image fusion program, which is embedded in Varian Eclipse™ treatment planning system. It was found with the fixed points method (three non collinear points were used) that $$\begin{pmatrix} x^{T \leftarrow P} \\ y^{T \leftarrow P} \\ z^{T \leftarrow P} \end{pmatrix}$$

is equal to $$\begin{pmatrix} -1.936 \text{ cm} \\ -1.251 \text{ cm} \\ -1.719 \text{ cm} \end{pmatrix}$$

and $$\begin{pmatrix} \theta_x \\ \theta_y \\ \theta_z \end{pmatrix}$$

is equal to $$\begin{pmatrix} -3.59 \text{ degree} \\ 5.82 \text{ degree} \\ 6.86 \text{ degree} \end{pmatrix}$$

By applying equations 10 through 16, the new beam parameters for fully correcting the shift were derived and are set forth in Table 2. The corresponding beam portals are displayed in FIGS. 4a_b, 4b_b, and 4c_b for field 1, field 2 and field 3, respectively. FIGS. 4a_a, 4b_a, and 4c_a are identical to FIGS. 3a_a, 3b_a and 3c_a, respectively, and were repeated so that the corrected beam portals could be conveniently compared with those planned beam portals. As shown in the figures and the comparisons (between FIG. 4a_a and 4a_b, between FIG. 4b_a and 4b_b and between 4c_a and 4c_b), the corrected beam portals are very similar to the corresponding planned beam portals.

TABLE 1

Gantry, collimator, table and iso-center information for the use of three planned beams in the phantom case (IEC convention).

| Beam | Gantry Angle (degree) | Collimator Angle (degree) | Table Angle (degree) | Iso-center (cm) |
|---|---|---|---|---|
| Field 1 | 120.0 | 82.4 | 0.0 | (−1.7, 1.6, −1.4) |
| Field 2 | 286.5 | 281.3 | 0.0 | (−1.7, 1.6, −1.4) |
| Field 3 | 210.6 | 0.0 | 0.0 | (−1.7, 1.6, −1.4) |

TABLE 2

Derived gantry, collimator, table and iso-center information for the three beams (IEC convention). With the derived beam parameters, the detected target shift should be fully (six degree) corrected.

| Beam | Gantry Angle (degree) | Collimator Angle (degree) | Table Angle (degree) | Iso-center (cm) |
|---|---|---|---|---|
| Field 1 | 131.5 | 76.9 | 8.5 | (−4.2, −0.2, −2.9) |
| Field 2 | 298.0 | 285.9 | 10.0 | (−4.2, −0.2, −2.9) |
| Field 3 | 222.4 | 6.1 | 16.7 | (−4.2, −0.2, −2.9) |

While presently preferred embodiments of the invention has been described in particularity, the invention may be otherwise embodied within the scope of the appended claims.

What is claimed is:

1. A method for aligning radiotherapeutic beams from a generator thereof to a patient location that is linearly translatable along and rotatable around x, y, and z axes to correct for any radiotherapeutic beam deviations between a planned patient beam dosimetric treatment coordinate and an actual patient beam dosimetric treatment coordinate, comprising the steps of
   a. transforming at least one beam coordinate of a radiotherapeutic beam generation coordinate system to said planned patient beam dosimetric treatment coordinate system to provide a transformed patient beam generation coordinate system;
   b. transforming at least one of said beams from said planned patient beam dosimetric treatment coordinate system to a patient beam dosimetric treatment coordinate system identified at the time of patient treatment; and
   c. transforming at least one of said beams of said transformed patient beam dosimetric treatment coordinate system to said transformed beam generation coordinate system to provide an actual patient beam generation coordinate system for radiotherapeutic treatment and adjusting the radiotherapeutic beam generation to said patient treatment location as determined by said transformations.

2. A method as set forth in claim 1 wherein said step of transforming between room coordinate system and said patient beam dosimetric treatment coordinates where $$T^{P \leftarrow M} = \begin{pmatrix} \cos \Omega^P & -\sin \Omega^P & 0 \\ \sin \Omega^P & \cos \Omega^P & 0 \\ 0 & 0 & 1 \end{pmatrix} \quad (3)$$

is the rotational transformation matrix from the room coordinate system to the planned patient coordinate system in the planned patient geometry when the table angle in the plan is $\Omega^P$ and $$T^{P \leftarrow M} = \begin{pmatrix} \cos \Omega^P & \sin \Omega^P & 0 \\ -\sin \Omega^P & \cos \Omega^P & 0 \\ 0 & 0 & 1 \end{pmatrix} \quad (9)$$

is the rotational transformation matrix from the treatment patient coordinate system to the room coordinate system when the treatment couch angle in the treatment is $\Omega^T$ and where $$\begin{pmatrix} x^{M \leftarrow T} \\ y^{M \leftarrow T} \\ z^{M \leftarrow T} \end{pmatrix}$$

are the coordinates of the origin of the treatment patient coordinate system in the room coordinate system.

3. A method as set forth in claim 1 wherein the isocenter of the beam is $$\vec{r}_{iso}^M = \begin{pmatrix} 0 \\ 0 \\ 0 \end{pmatrix}$$

in the room coordinate system and in the planned patient beam dosimetric, the isocenter of the beam in said planned patient treatment coordinate is $$\begin{pmatrix} x_{iso}^T \\ y_{iso}^T \\ z_{iso}^T \end{pmatrix} = \begin{pmatrix} x^{T \leftarrow P} \\ y^{T \leftarrow P} \\ z^{T \leftarrow P} \end{pmatrix} + T^{T \leftarrow P} \otimes \left\{ \begin{pmatrix} x^{P \leftarrow M} \\ y^{P \leftarrow M} \\ z^{P \leftarrow M} \end{pmatrix} + T^{P \leftarrow M} \otimes \begin{pmatrix} 0 \\ 0 \\ 0 \end{pmatrix} \right\},$$

and where $$= \begin{pmatrix} x^{T \leftarrow P} \\ y^{T \leftarrow P} \\ z^{T \leftarrow P} \end{pmatrix} = \vec{\delta}_{iso}$$

and $\vec{\delta}_{iso}$ is isocenter a shift, and $\vec{B}_{G,p}^M$, $\vec{B}_{C,p}^M$ and $\vec{B}_{T,p}^M$ represent the angular positions of said beam generator, a collimator, and a couch in said room coordinates in said planned patient treatment coordinates, and wherein $$\vec{B}_{G,p}^M = \begin{pmatrix} \sin\Theta_p \\ 0 \\ \cos\Theta_p \end{pmatrix}, \vec{B}_{C,p}^M = \begin{pmatrix} \cos\Theta_p \sin\Phi_p \\ -\cos\Phi_p \\ -\sin\Theta_p \sin\Phi_p \end{pmatrix}, \vec{B}_{T,p}^M = \begin{pmatrix} -\sin\Omega_p \\ -\cos\Omega_p \\ 0 \end{pmatrix} \quad 5$$

where $\Theta_p$, $\Phi_p$ and $\Omega_p$ are the angles of the beam generator, collimator and the couch angles in the planned patient treatment and said beam generator parameters in the room coordinate system in the treatment are:

$$\vec{B}_{G,t}^M = T^{M \leftarrow T} T^{T \leftarrow P} T^{P \leftarrow M} \vec{B}_{G,p}^M$$

$$\vec{B}_{C,t}^M = T^{M \leftarrow T} T^{T \leftarrow P} T^{P \leftarrow M} \vec{B}_{C,p}^M$$

where $$\vec{B}_{G,t}^M = \begin{pmatrix} \cos\Omega_t & \sin\Omega_t & 0 \\ -\sin\Omega_t & \cos\Omega_t & 0 \\ 0 & 0 & 1 \end{pmatrix} \otimes T^{T \leftarrow P} \otimes \begin{pmatrix} \cos\Omega_p & -\sin\Omega_p & 0 \\ \sin\Omega_p & \cos\Omega_p & 0 \\ 0 & 0 & 1 \end{pmatrix} \otimes$$

$$\begin{pmatrix} \sin\Theta_p \\ 0 \\ \cos\Theta_p \end{pmatrix}$$

$$= \begin{pmatrix} \cos\Omega_t & \sin\Omega_t & 0 \\ -\sin\Omega_t & \cos\Omega_t & 0 \\ 0 & 0 & 1 \end{pmatrix} \otimes T^{T \leftarrow P} \otimes \begin{pmatrix} \cos\Omega_p \sin\Theta_p \\ \sin\Omega_p \sin\Theta_p \\ \cos\Theta_p \end{pmatrix}$$

$$\vec{B}_{C,t}^M = \begin{pmatrix} \cos\Omega_t & \sin\Omega_t & 0 \\ -\sin\Omega_t & \cos\Omega_t & 0 \\ 0 & 0 & 1 \end{pmatrix} \otimes T^{T \leftarrow P} \otimes \begin{pmatrix} \cos\Omega_p & -\sin\Omega_p & 0 \\ \sin\Omega_p & \cos\Omega_p & 0 \\ 0 & 0 & 1 \end{pmatrix} \otimes$$

$$\begin{pmatrix} \cos\Theta_p \sin\Phi_p \\ -\cos\Phi_p \\ -\sin\Theta_p \sin\Phi_p \end{pmatrix}$$

-continued $$= \begin{pmatrix} \cos\Omega_t & \sin\Omega_t & 0 \\ -\sin\Omega_t & \cos\Omega_t & 0 \\ 0 & 0 & 1 \end{pmatrix} \otimes T^{T \leftarrow P} \otimes$$

$$\begin{pmatrix} \cos\Omega_p \cos\Theta_p \sin\Phi_p + \sin\Omega_p \cos\Phi_p \\ \sin\Omega_p \cos\Theta_p \sin\Phi_p - \cos\Omega_p \cos\Phi_p \\ -\sin\Theta_p \sin\Phi_p \end{pmatrix}$$

where $\Theta_t$, $\Phi_t$ and $\Omega_t$ are the respective corrected angles of the beam for said planned patient treatment.

4. A method as set forth in claim 3 wherein $\vec{B}_{G,t}^M$ is parallel to x-z plane of the beam generation coordinate system and angle $\Omega_t$ is determined by equations $$\vec{B}_{G,t}^M \cdot \vec{j}^M = 0 \text{ and} \quad (14a)$$

$$\Omega_t = \arctan\left(\frac{a_{21}\cos\Omega_p \sin\Theta_p + a_{22}\sin\Omega_p \sin\Theta_p + a_{23}\cos\Theta_p}{a_{11}\cos\Omega_p \sin\Theta_p + a_{12}\sin\Omega_p \sin\Theta_p + a_{13}\cos\Theta_p}\right) \cdot 2 \quad (14b)$$

and where angle $\Theta_t$ is determined by equations:

$$\Theta_t = \begin{cases} \arccos(\vec{B}_{G,t}^M \cdot \vec{k}^M) & \text{if } (\vec{B}_{G,t}^M \times \vec{k}^M) \cdot \vec{j}^M \leq 0 \\ 360 - \arccos(\vec{B}_{G,t}^M \cdot \vec{k}^M) & \text{if } (\vec{B}_{G,t}^M \times \vec{k}^M) \cdot \vec{j}^M > 0 \end{cases} \quad (15)$$

and angle $\Phi_t$ is determined by equations:

$$\Phi_t = \begin{cases} 180 - \arccos(\vec{B}_{C,t}^M \cdot \vec{j}^M), & \text{if } (\vec{B}_{C,t}^M \times \vec{j}^M) \cdot \vec{B}_{G,t}^M \geq 0 \\ 180 + \arccos(\vec{B}_{C,t}^M \cdot \vec{j}^M), & \text{if } (\vec{B}_{C,t}^M \times \vec{j}^M) \cdot \vec{B}_{G,t}^M < 0 \end{cases} \quad (16)$$

\* \* \* \* \*